United States Patent [19]
Downs et al.

[11] Patent Number: 5,830,324
[45] Date of Patent: *Nov. 3, 1998

[54] CONTROLLED CONTINUOUS PURIFICATION OF PROPYLENE OXIDE BY EXTRACTIVE DISTILLATION

[75] Inventors: James Joseph Downs; Andrew Charles Hiester, both of Kingsport, Tenn.; Mark Elliott Taylor, Orange; Mark Allan Mueller, Austin, both of Tex.; Michael Warren Peters, Gilbert, Ariz.; William Pleasie Nelson, Nederland, Tex.

[73] Assignee: Huntsman Specialty Chemicals Corp., Austin, Tex.

[ * ] Notice: The term of this patent shall not extend beyond the expiration date of Pat. No. 5,464,505.

[21] Appl. No.: 733,696

[22] Filed: Oct. 17, 1996

Related U.S. Application Data

[63] Continuation of Ser. No. 378,291, Jan. 25, 1995, abandoned.

[51] Int. Cl.⁶ .............................. B01D 3/40; B01D 3/42; C07D 301/32
[52] U.S. Cl. .................. 203/1; 203/2; 203/3; 203/14; 203/62; 203/64; 549/541
[58] Field of Search .................................. 203/1, 3, 64, 2, 203/14, 62, 78, 80, DIG. 9, DIG. 18, DIG. 23; 549/541

[56] References Cited

U.S. PATENT DOCUMENTS

| | | | |
|---|---|---|---|
| 3,632,482 | 1/1972 | Hoory | 203/62 |
| 3,715,284 | 2/1973 | Burns et al. | 203/62 |
| 4,971,661 | 11/1990 | Meyer et al. | 203/62 |
| 5,116,465 | 5/1992 | Yeakey et al. | 203/64 |
| 5,145,563 | 9/1992 | Culbreth, III et al. | 203/64 |
| 5,464,505 | 11/1995 | Peters et al. | 203/64 |

*Primary Examiner*—Virginia Manoharan
*Attorney, Agent, or Firm*—Russell R. Stolle; Ron D. Brown; Carl G. Ries

[57] ABSTRACT

In the continuous purification of a propylene oxide feedstock contaminated with water, methanol and acetone wherein an acetone buffer is established in the column, normal distillation conditions are maintained or restored during or after an upset by continuously monitoring predetermined distillation conditions in the acetone buffer zone, and adding additional acetone to the extractive distillation column when the monitored distillation condition deviates from a predetermined value by a predetermined amount.

19 Claims, 2 Drawing Sheets

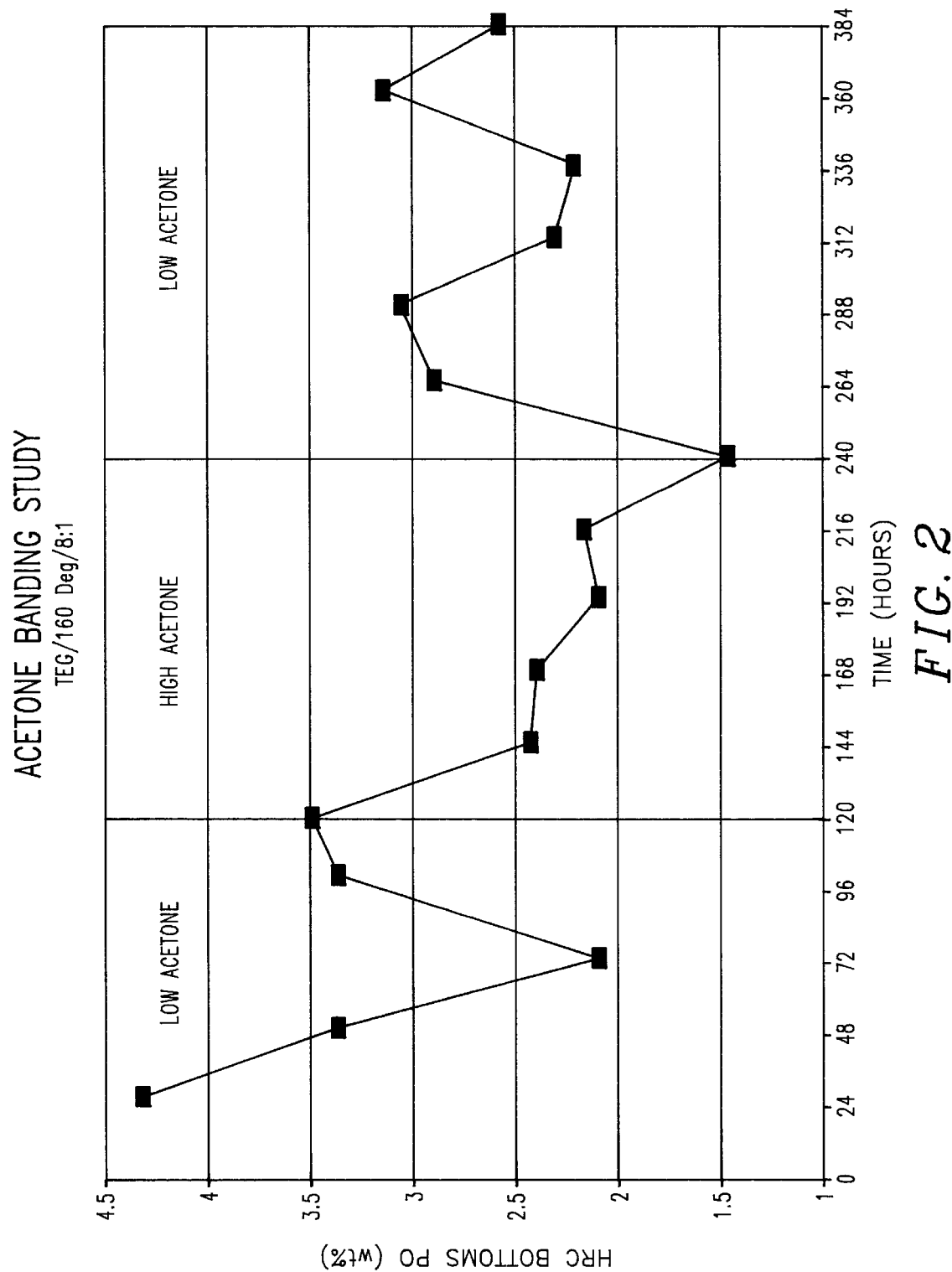

CONTROLLED CONTINUOUS PURIFICATION OF PROPYLENE OXIDE BY EXTRACTIVE DISTILLATION

This application is a continuation of application Ser. No. 08/378,291 filed Jan. 25, 1995 now abandoned.

BACKGROUND OF THE INVENTION

1. Technical Field of the Invention

This invention relates to the controlled continuous purification of propylene oxide. More particularly, this invention relates to a distillation process for continuously removing contaminating quantities of impurities including oxygen-containing impurities such as methanol, acetone and water from an impure propylene oxide feedstock. Still more particularly, this invention relates to a method for counteracting upsets when an impure propylene oxide feedstock, such as a feedstock contaminated with from about 50 to about 4,000 ppm of methanol, from about 0.01 to about 2 wt. % of water and from about 0.01 to about 2 wt. % of acetone is continuously purified in an extractive distillation column using oxyalkylene glycols as extractive distillation agents. Desirably, the acetone concentration will be in the range of about 0.4 to about 1.5 wt. %

2. Prior Art a. General Background Information

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol, acetone and water are common contaminants for propylene oxide which are removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

b. Extractive Distillation Background

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50–55 that: "Propylene oxide, however, has a substantial solubility in water and is readily hydrolyzed to propylene glycol (PG) in the presence of large amounts of water"—i.e., in the reboiler section of the tower.

Meyer et al. U.S. Pat. No. 4,971,661 discloses the use of an aqueous acetone extraction to remove methanol from propylene oxide.

Meyer et al. point out that the presence of additional acetone (added to feed or solvent) serves as a buffer between the reboiler section and the balance of the tower. This is apparent if one looks at the normal boiling points (i.e., atmospheric pressure):

| Component | NBP (°C.) |
|---|---|
| Propylene Oxide (PO) | 34 |
| Acetone | 56 |
| Water | 100 |

The acetone serves as a buffer section in the tower between the PO and water (a high concentration of water is in the reboiler and a high concentration of PO is above the acetone buffer zone). The acetone buffer zone limits the contact of PO with a high concentration of water. It is apparent that the additional acetone makes its presence known in the reboiler as well as evidenced by lower reboiler temperatures. This also helps reduce PO to PG conversion as the reaction rate increases with increasing temperature. Any PO making its way to the reboiler will see a lower temperature, thus reducing its conversion to PG.

It is clear that the tower should be operated at as low a pressure as is practical to minimize PO loss.

Yeakey et al. disclose the use of 2-hydroxyethyl 2-hydroxyethyl carbamate as an extractive distillation agent for the removal of water from impure propylene oxide in U.S. Pat. No. 5,116,465.

U.S. Pat. No. 5,116,466 to Marquis et al. discloses that one may use 1-methyl-2-pyrrolidinone as an extractive distillation agent to remove water, acetone and methanol from propylene oxide contaminated with these impurities.

U.S. Pat. No. 5,116,467 to Marquis et al. discloses the use of sulfolane as an extractive distillation agent to remove water from propylene oxide.

c. Glycol and Glycol Ether Extractants

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent. It is stated that the concentration of the solvent in the vapor space in the extractive distillation zone of the extractive distillation tower should preferably be between 15 and 50 mole percent of the total vapor.

Shih et al. U.S. Pat. No. 5,000,825 discloses the purification of monoepoxides such as propylene oxide that are contaminated with oxygenated impurities such as water, low molecular weight alcohols, low molecular weight ketones, low molecular weight aldehydes and the like by the extractive distillation of the contaminated monoepoxide using a lower glycol containing 2 to 4 carbon atoms. Examples of the lower glycols that are given in the patent include ethylene glycol, 1,2-propane diol, 1,3-propane diol, 1,4-butane diol, 1,2-butane diol, 1,3-butane diol, 1,4-butane diol, butane diol and 2,3-butane diol. It is stated that higher diols or higher glycol ethers do not provide sufficient selectivity for the removal of impurities and they are not included in the list of extractive distillation solvents suitable for use in the invention.

In Marquis et al. U.S. Pat. No. 5,139,622 the use of triethylene glycol is disclosed for the removal of methanol, acetone and water from propylene oxide contaminated with these impurities.

Marquis et al. U.S. Pat. No. 5,154,803 discloses the use of 2-methyl-2,4-pentane diol as an extractive distillation agent in the removal of methanol, acetone and water from propylene oxide contaminated with these impurities.

Marquis et al. U.S. Pat. No. 5,154,804 discloses the use of monohydroxy alkoxy alkanols containing 5 to 8 carbon atoms as extractive distillation agents in the removal of methanol, acetone and water from propylene oxide contaminated with these impurities.

The use of dipropylene glycol as an extractive distillation agent for the removal of methanol, acetone and water from propylene oxide contaminated with these impurities is disclosed in Marquis et al. U.S. Pat. No. 5,160,587.

In copending and coassigned Peters et al. U.S. patent application Ser. No. 08/251,158, filed May 31, 1994 (D#81,307), now U.S. Pat. No. 5,433,160 and entitled "Use of Propylene Oxide Adducts in the Purification of Propylene Oxide by Extractive Distillation" the use of propylene oxide adducts of oxyethylene glycols as extractive distillation agents is disclosed.

In copending and coassigned Peters et al. U.S. patent application Ser. No. 08/251,151, filed May 31, 1994 (D#81,309), now U.S. Pat. No. 5,433,160 and entitled "Use of Mixed Polyoxypropylene Glycols in the Extractive Distillation of Propylene Oxide" the use of mixed polyoxypropylene glycols as extractive distillation agents is disclosed.

SUMMARY OF THE INVENTION

In accordance with the present invention, an impure propylene oxide feedstock, such as a feedstock contaminated with 0.01 to 2 wt. % of water, from about 50 to about 4,000 ppm of methanol and containing from about 0.1 to about 2 wt. % of acetone, and more preferably about 0.4 to about 0.5 wt. % of acetone, is continuously charged to the lower half of an extractive distillation column containing at least about 10 theoretical plates and an oxyalkylene glycol extractive distillation agent is continuously charged to the tower at a point at least 4 stages above the impure propylene oxide feed point. Preferably, the extractive distillation tower will contain from about 30 to about 120 theoretical plates and the extractive distillation agent will be charged to the tower at a point of from 7 to 50 theoretical stages above the impure propylene oxide feed point. The extractive distillation agent is introduced into the extractive distillation column in the ratio of said feedstock to said extractive distillation agent of from about 1:1 to about 20:1, and more preferably 2:1 to 10:1, whereby a light distillate fraction is continuously obtained consisting essentially of propylene oxide contaminated with trace amounts of water, methanol and acetone, such as about 5 to about 600 ppm of water, about 15 to 2,000 ppm of methanol and about 0.1 to about 100 ppm of acetone.

The extractive distillation conditions of temperature, pressure and acetone feed concentration should be correlated so as to establish an acetone buffer in the extractive distillation column at a point below the point of introduction of the impure feedstock. One or more of the distillation conditions in the acetone buffer are continuously monitored to detect a deviation from a predetermined value sufficient to indicate that an upset in continuous distillation conditions has occurred or is occurring and additional acetone is added to the distillation column (together with or separately from the impure feedstock) in an amount sufficient to maintain or reestablish the buffer zone.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because the water present in the propylene oxide will tend to react with the propylene oxide to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene oxide with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a heavy distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone.

As mentioned above, it has heretofore been proposed to use oxyalkylene glycols as extractive distillation agents in the continuous extractive distillation of an impure propylene oxide feedstock contaminated with water, methanol and acetone.

It has also been heretofore noted that if acetone is present in the feed or added to the column, an acetone buffer will form in the extractive distillation column and will be located in the column above the reboiler and below the point of introduction of the impure feed. Thus, over a period of time (e.g., from about 5 to 24 hours of operation) the acetone charged to the extractive distillation column will tend to become concentrated at a point or zone in the column above the reboiler outlet line and the impure propylene oxide feed point, forming a detectable acetone buffer. Water concentration is comparatively high in the reboiler, where distillation temperatures are also the highest. As a consequence, there is a tendency for propylene glycol to form by the high temperature hydration of the propylene oxide and this represents a net loss of propylene oxide for the process. More importantly, under the mildly acidic conditions that prevail in the distillation column, propylene oxide can react with the oxyalkylene glycol extractive distillation agent to form a propylene oxide adduct. The adduct is effective as an extractive distillation agent, but also represents a net loss of propylene oxide.

Over a period of time (e.g., from about 1.0 to about 200.0 hours of operation) the acetone charged to the extractive distillation column will tend to become concentrated at a point or zone in the column above the reboiler outlet line and the impure propylene oxide feed point, forming a detectable acetone buffer.

The acetone buffer prevents the propylene oxide from propagating downward through the column toward the reboiler by altering vapor and liquid equilibrium conditions. Specifically, due to the higher boiling point of acetone relative to propylene oxide, the propylene oxide will preferentially fractionate to locations higher in the column than the acetone band. This prevents the propylene oxide from propagating to locations low in the column, specifically the column reboiler, where the propylene oxide would be undesirably lost from the system.

From time to time tower upsets occur in the extractive distillation column for a variety of unintended reasons, such as unexpected pressure surges, unexpected temperature drops, unexpected changes in extractive distillation agent volume, an unexpected decrease in the concentration of acetone in the feed, unexpected changes in feed rate, changes in weather conditions, loss of solvent, etc. When upsets (i.e., unanticipated deviations) in distillation conditions occur, the acetone in the distillation column may move downwardly into the reboiler or upwardly into the reflux condenser (depending on the nature of the upset), thus eliminating the acetone buffer. The acetone buffer will not immediately form when normal distillation conditions are established, as noted above. During the period of operations when the buffer is forming, significant losses of propylene oxide to propylene glycol and/or alkylene glycol adducts can occur.

The existence and location of the acetone buffer can be determined for a particular distillation column by running a temperature profile of the column to locate the point in the column where the distillation temperature approximates the boiling point of acetone at the pressure there prevailing, by taking and analyzing samples along the length of the column, etc. Once the location of the acetone buffer is located, appropriate sensors, such as temperature probes, pressure probes, product sample lines, etc., can be appropriately installed in the column and an allowable deviation from the predetermined normal operating conditions can be calculated.

In accordance with the present invention, a source of acetone (e.g., a drum) is located adjacent to the continuous extractive distillation column and is connected with the impure propylene oxide feed line through a feed line controlled by a remotely controllable control valve. The output of the sensor on the column can then be operatively interconnected with the control valve on the acetone feed line and the control valve can be set to automatically open on receipt of a signal indicating that an upset has occurred or is occurring. The remotely controlled valve then opens to rapidly charge a predetermined amount of acetone to the distillation column in order to maintain or rapidly reestablish the acetone buffer.

The Oxyalkylene Glycol Extractive Distallation Agents

In conducting the extractive distillation process of the present invention, any of the suitable known alkylene glycol extractive distillation agents can be used, such as propylene glycol, dipropylene glycol, tripropylene glycol, ethylene glycol, diethylene glycol, triethylene glycol, etc., or propylene oxide adducts thereof.

When propylene oxide is reacted with an oxyethylene glycol to provide a propylene oxide adduct of the oxyethylene glycol, the reaction product will actually comprise a mixture of isomers. For example, when one mole of propylene oxide is reacted with one mole of ethylene glycol, two isomers will be formed, as follows:

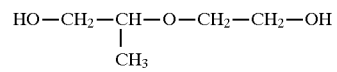

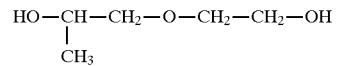

In like fashion, when two moles of propylene oxide reacts with ethylene oxide, an even more complex mixture of isomers is formed, i.e.:

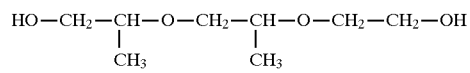

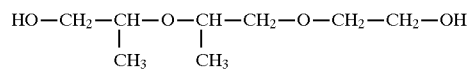

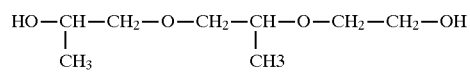

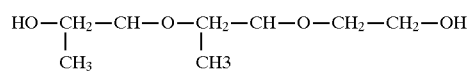

Accordingly, the mixed propylene oxide adducts of oxyethylene glycols that may be used as extractive distillation agents in accordance with the present invention may be defined as a mixture having the formula

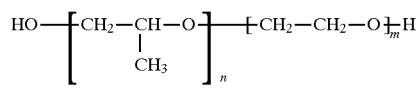

wherein n is a positive integer having a value of 1 to about 4, m is a positive integer having a value of 1 to 3 and the mixture having an average molecular weight of about 250 to 350.

In like fashion, when propylene oxide is reacted with propylene glycol to provide di-propylene glycol, the reaction product will actually comprise a mixture of isomers, as follows:

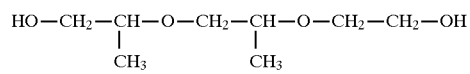

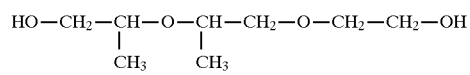

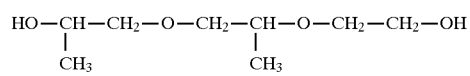

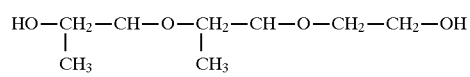

-continued

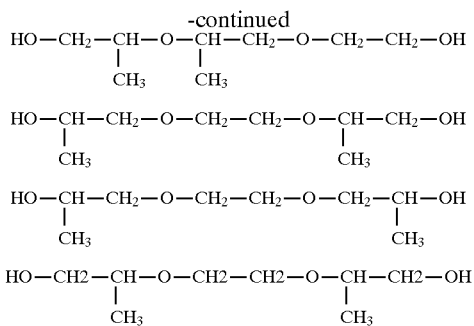

Thus, when propylene oxide reacts with dipropylene glycol to form tripropylene glycol, a mixture of isomeric tripropylene glycol isomers will be formed.

Accordingly, the mixture of polyoxypropylene glycols that may be used as extractive distillation agents in accordance with the present invention may be defined as a mixture having the formula:

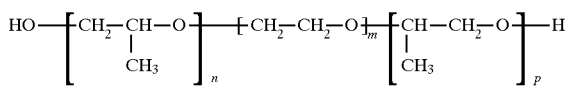

wherein n and p are positive integers, m is a positive integer having a value of 1 to 3, the sum of n and p has a value of 1 to about 4, and the mixture having an average molecular weight of about 250 to 350.

When the extractive distillation process of the present invention is to be practiced on a continuous basis, the mixture of polyoxyalkylene glycols can be formed in situ by initially charging ethylene glycol, diethylene glycol, triethylene glycol propylene glycol or dipropylene glycol to the extractive distillation tower. Thereafter, propoxylation of the initially charged oxyethylene glycol will occur, as described above and over the passage of time (e.g., about 100 hours of continuous operations) a mixture of polyoxypropylene glycols will be formed that will have the composition described above.

During prolonged continuous operations of about 1,000 hours or more, or because of upsets in the extractive distillation column, the amount of heavier propylene oxide adducts having molecular weights in excess of about 600 may increase to an extent such that the efficiency of the continuous extractive distillation operation deteriorates. If undesirably high levels of contaminants appear in the purified propylene oxide product, the problem can be solved by purging all or part of the extractive distillation agent from the system.

For example, about 0.1 to about 15 vol. % per hour of the total volume of circulating solvent may be removed and replaced with an equivalent volume of fresh solvent, a circulating stream of solvent can be obtained in which not more than about 5 to about 35 wt. % of the circulating stream of solvent will have a molecular weight of more than about 250.

During continuous operations of about 1,000 hours or more, and because of upsets in the extractive distillation column, the amount of heavier propylene oxide adducts having molecular weights in excess of about 350 may increase to an extent such that the efficiency of the continuous extractive distillation operation deteriorates. When undesirably high levels of contaminants appear in the purified propylene oxide product, the problem can be solved by purging part of the circulating stream of extractive distillation agent from the system and replacing it with an equivalent volume of fresh oxyethylene glycol extractive distillation solvent.

Thus, when conducting continuous distillation operations in accordance with the preferred embodiment of the present invention, from about 0.1 to about 15 vol. % per hour of the total volume of circulating solvent is removed and replaced with an equivalent volume of fresh solvent, the amount being adjusted to provide a circulating stream of solvent having an average molecular weight of not more than about 350, such as an average molecular weight of about 250 to about 350.

Figure 1:
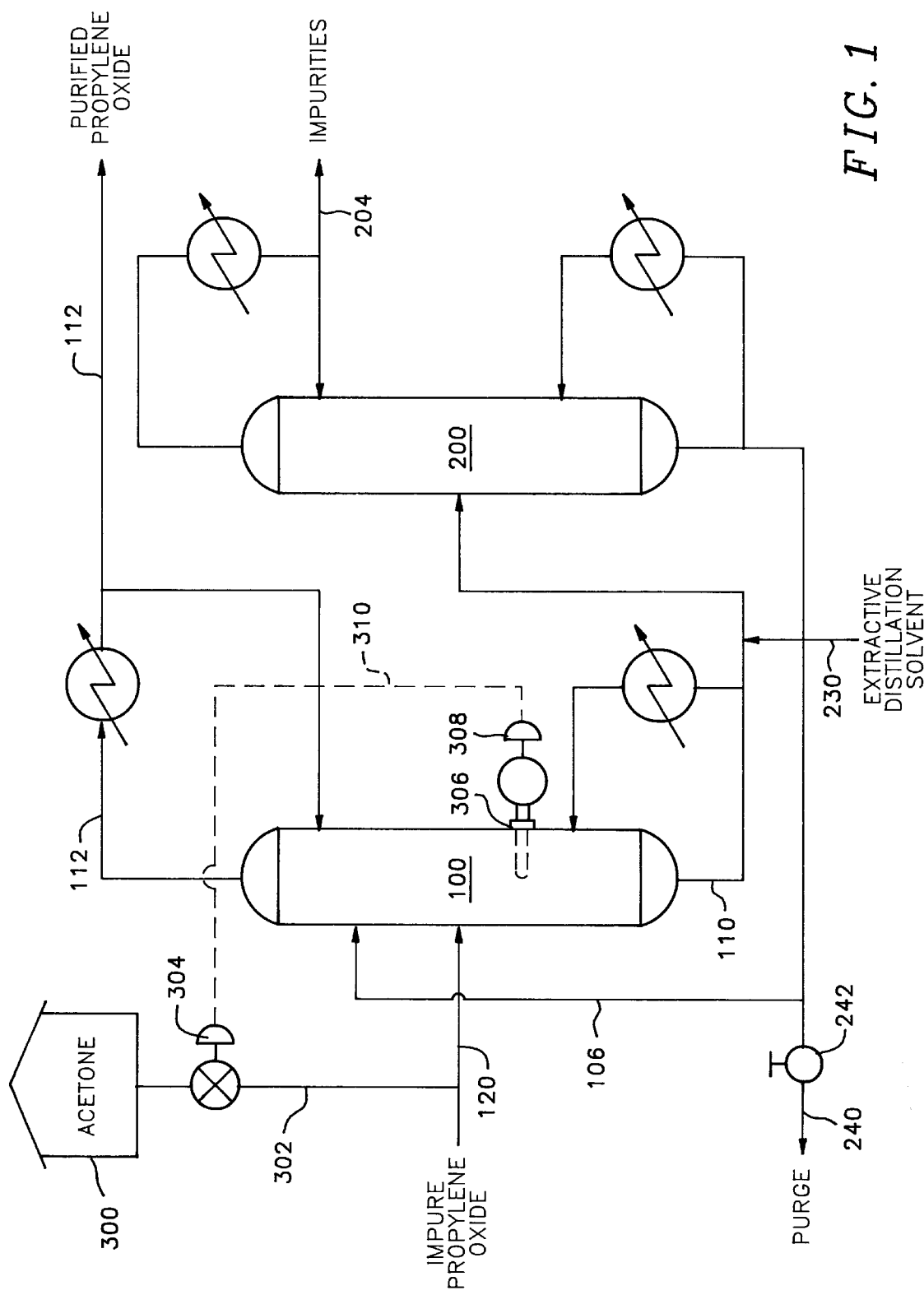
FIG. 1, is a schematic flow sheet with conventional parts omitted showing the general recovery sequence that is used in accordance with the present invention in purifying propylene oxide.

In the drawing, for convenience, the present invention is illustrated in connection with a process wherein the propylene oxide is prepared by the epoxidation of propylene with tertiary butyl hydroperoxide in solution in tertiary butyl alcohol to provide a reaction product comprising propylene oxide and additional tertiary butyl alcohol.

FIG. 2 is a chart showing the influence of an acetone buffer on the concentration of propylene oxide at the bottom of a distillation column.

DESCRIPTION OF THE PREFERRED EMBODIMENT

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, etc., have been omitted.

In accordance with a preferred embodiment of the present invention, propylene oxide is separated in a preliminary distillation zone (not shown) from other components of an epoxidation reaction mixture in order to provide an impure propylene oxide fraction contaminated with oxygen-containing impurities such as acetone, methanol, water, etc.

The impure propylene oxide feedstock that is thus obtained in the preliminary distillation zone is then purified in a propylene oxide purification distillation zone, which in accordance with the preferred embodiment of the present invention, comprises two distillation columns, each of which is equipped with an appropriate reflux condensing means and an appropriate reboiler heating means.

In accordance with the present invention, an impure propylene oxide feedstock fraction, such as a fraction contaminated with from about 50 to about 4,000 ppm of methanol, and containing from about 0.1 to about 2 wt. % of acetone (e.g., 0.4 to 1.5 wt. %) and about 0.01 to about 2 wt. % of water and other oxygen-containing impurities is charged by way of a line 120 leading to a distillation column 100 which, in accordance with the present invention, will preferably be a column containing at least about 10 theoretical plates, more preferably at least 25 theoretical plates and still more preferably, from about 30 to about 100 theoretical plates. The column 100 is suitably operated under distillation conditions including a pressure of about 10 to 40 psia, a reflux ratio of from about 2:1 to about 10:1, a reboiler temperature within the range of about 1000 to about 250° C.

(e.g., 210° C.) and a top temperature of about 200 to about 80° C. (e.g., about 20° C.).

The impure propylene oxide is preferably charged to the distillation column 100 in the lower half thereof. An extractive distillation agent comprising an oxyalkylene glycol is charged to the upper half of the distillation column 100 by an extractive distillation charge line 106.

A purified propylene oxide fraction, such as a fraction containing about 100 ppm or less of water, is removed from the column 100 as a light distillation fraction 112, the purified propylene oxide in the line 112 containing significantly reduced amounts of methanol and acetone, such as about 15 to 900 ppm of methanol and about 0.01 to 100 ppm of acetone. A heavier fraction 110 is withdrawn from the distillation column 100 which contains substantially all of the extractive distillation agent charged by the line 106 and also substantially all of the water, acetone and other oxygen-containing impurities introduced into the column 100 with the impure propylene oxide 120.

The heavier distillation fraction 110 from the column 100 comprising water, methanol, acetone, tertiary butyl alcohol and other impurities and extractive distillation agent is charged to a second distillation column 200 wherein light impurities such as methanol, acetone, water, etc., are separated overhead as a distillation fraction 204 that is discharged from the system for any suitable use, such as for use as a steam boiler feedstock or for recovery.

A heavier distillation fraction 106 is discharged from the distillation column 200 comprising extractive distillation agent which is recycled to distillation column 100 by line 106.

Fresh extractive distillation agent, either as the original charge, or as make-up solvent, is introduced into the system by a branch line 230 leading to the charge line 110 for the second distillation column 200 so that any water introduced into the system with the fresh extractive distillation agent will be separated therefrom in the column 200 and withdrawn from the column 200 through the line 204.

From about 0.1 to about 15 vol. % per hour of the total volume of circulating solvent is removed by line 240 controlled by valve 242 and replaced with an equivalent volume of fresh solvent introduced by way of line 230 the amount being adjusted to provide a circulating stream of solvent having an average molecular weight of not more than about 350, such as an average molecular weight of about 250 to about 350.

In accordance with the present invention, the portion of the column 100 containing the acetone buffer is located (e.g., by running a temperature profile of the column 100 to locate the point in the column 100 where the temperature in the column 100 is about the same as the boiling point of acetone at the pressure at that point in the column 100.

A sensing element, such as a temperature probe 306 is mounted on the column 100 at that point and is operatively interconnected with a monitor 308. An acetone storage tank 300 is provided, and the acetone storage tank 300 is connected with the impure propylene oxide charge line 120 by a line 302 having a control valve 304 mounted therein, the control valve 304 being normally closed and being regulated by an actuator 304 operatively connected by a lead 310 with a monitor 308.

The temperature probe 306 will detect the temperature at that point in the distillation column 100. The monitor is set to transmit a signal through the lead 310 to the control valve 304 when the distillation condition being monitored (e.g., temperature) indicates that an upset has occurred or is occurring. When this happens, the valve 304 is opened to permit the flow of acetone to the propylene oxide feed line 120 through acetone charge line 302. Acetone will be charged in an amount sufficient to permit a rapid maintenance or restoration of the acetone buffer. For example, about 0.5 wt. % of acetone, based on impure propylene oxide being charged through the feed line 120 can be charged through the line 302 until the sensor 306 detects the restoration of the predetermined distillation variable (e.g. temperature). At that time, a signal will be transmitted from the monitor 308 to the control valve 304 and the valve 304 will be closed, thus terminating the flow of acetone through the line 302. Normal distillation conditions are thus reestablished.

EXAMPLES

The invention will be further illustrated by the following specific examples which are given by way of illustration and not as limitations on the scope of this invention. Where parts are mentioned, they are parts by weight.

Example 1

A two-inch Oldershaw-type distillation column containing 120 actual trays was used in an extractive distillation to remove oxygenated impurities from two crude propylene oxide (PO) feed streams. The two crude PO streams differed only in that one stream contained a relatively large amount of acetone while the other contained no detectable amount of acetone. The purified PO was recovered as the overhead product from the first column and the solvent plus impurities made up the bottoms stream. A second one-inch stainless steel column packed with eleven feet of stainless steel wire mesh packing was used to purify the contaminated solvent which was then recycled from the bottoms of the second column to a point above the feed on the first column. The impurities removed from the solvent were recovered in the overhead of the second column. The solvent used was tri-ethylene glycol (TEG). The extractive distillation column was started up first using the crude PO which contained no acetone. After five days, the feed to the column was switched to the crude PO containing acetone. After five more days of operation the feed was switched back to the crude PO containing no acetone for a final five days. Table 1 shows the composition of the two crude propylene oxide feed streams. Table 2 shows the average composition of PO in the bottoms of the extractive distillation column during each feed cycle. A simple t-test at 95% confidence shows that the average PO concentration when there was acetone in the feed was lower than during the two cycles where there was no detectable acetone in the feed. This same test shows that there is no statistical difference between the PO concentrations during the two feed cycles with no acetone.

TABLE 1

| Feed Compositions | | |
|---|---|---|
|  | Crude PO Feed (no Acetone) | Crude PO Feed (with Acetone) |
| Acetaldehyde (ppm) | 210 | 210 |
| Methanol (ppm) | 2200 | 2200 |
| Methyl Formate (ppm) | 240 | 240 |
| Acetone (wt %) | ND | 1.8 |
| t-butyl alcohol (ppm) | 1200 | 1200 |
| water (ppm) | 1800 | 1800 |

TABLE 2

Average Bottoms PO Compositions

|  | No Acetone | With Acetone | No Acetone |
|---|---|---|---|
| PO (wt %) | 3.334 | 2.113 | 2.707 |
| Standard Deviation | 0.797 | 0.386 | 0.389 |

The data, as summarized in the drawings, demonstrates, statistically, that having acetone in the feed reduces the amount of propylene oxide in the bottoms fraction as compared to the case where there was no detectable acetone in the feed. The drawings also demonstrate, statistically, that the addition of acetone to the feed reduces the temperature in the propylene oxide bottoms fraction as compared to the case where there was no detectable acetone in the feed. This is important because the lower temperature results in less degradation of propylene oxide, thus improving yield.

The aberrant data points at 72, 312 and 336 hours reflect normal variability in column operations resulting, for example, from pressure and temperature fluctuations, fluctuations in upstream and downstream columns, and sampling and analysis.

Having thus described our invention, what is claimed is:

1. A continuous operation of an extractive distillation column for the purification of a propylene oxide feedstock contaminated with water, methanol and acetone which comprises the steps of continuously introducing said impure propylene oxide feedstock into a lower half of said extractive distillation column under predetermined distillation conditions of predetermined temperature, pressure and acetone feed concentration selected to promote formation and maintenance of an acetone buffer zone in the distillation column below the point of introduction of said impure propylene oxide feedstock, continuously introducing a recycle stream of an oxyalkylene glycol extractive distillation agent, or a propylene oxide adduct thereof into said extractive distillation column above said acetone buffer zone; continuously withdrawing a lighter distillation fraction consisting essentially of anhydrous propylene oxide contaminated with trace quantities of said acetone and methanol from said extractive distillation column above the point at which said oxyalkylene glycol extractive distillation agent or a propylene oxide adduct thereof is introduced; continuously withdrawing a heavier distillation fraction containing substantially all of the oxyalkylene glycol, water, acetone and methanol introduced into said extractive distillation column from the reboiler of said extractive distillation column; separately distilling said heavier distillation fraction and recycled oxyalkylene glycol extractive distillation agent to provide an overhead discard distillation fraction comprising methanol, acetone and water and a higher boiling recycle stream comprising said extractive distillation agent; purging a minor amount of said recycle stream and charging the remainder to said extractive distillation column as said recycle stream, maintaining or reestablishing the acetone buffer when tower upsets occur including continuously monitoring one of said distillation conditions in said extractive distillation column to detect an upset, and separately adding additional acetone to said impure propylene oxide feed stock being fed to said extractive distillation column in response to an upset in said distillation conditions in an amount sufficient to maintain or restore said acetone buffer zone.

2. An extractive distillation process as in claim 1 wherein the predetermined distillation conditions monitored in said extractive distillation column is temperature.

3. An extractive distillation process as in claim 1 wherein the predetermined distillation conditions monitored in said extractive distillation column is pressure.

4. An extractive distillation process as in claim 1 wherein the predetermined distillation conditions monitored in said extractive distillation column is acetone feed concentration.

5. An extractive distillation process as in claim 1 wherein the oxyalkylene glycol extractive distillation agent is a mixture of oxyalkylene glycols having molecular weights of not more than about 600 and wherein about 0.1 to about 15 vol. % per hour of the total volume of the extractive distillation agent is removed and replaced with an equivalent volume of fresh solvent.

6. An extractive distillation process as in claim 5 wherein the extractive distillation agent consists essentially of a mixture of propylene oxide adducts of oxyethylene glycols having the formula:

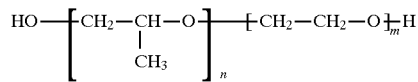

wherein n is a positive integer having a value of 1 to about 4, m is a positive integer having a value of 1 to 3 and the mixture has an average molecular weight of about 250 to 350.

7. An extractive distillation process as in claim 6 wherein the extractive distillation agent consists essentially of a mixture of propylene oxide adducts of ethylene glycol.

8. An extractive distillation process as in claim 6 wherein the extractive distillation agent consists essentially of a mixture of propylene oxide adducts of diethylene glycol.

9. An extractive distillation process as in claim 6 wherein the extractive distillation agent consists essentially of a mixture of propylene oxide adducts of triethylene glycol.

10. An extractive distillation process as in claim 6 wherein the extractive distillation agent consists essentially of a mixture of polyoxypropylene glycols having the formula:

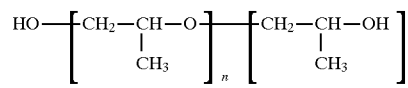

wherein n is a positive integer having a value of 1 to about 4, the mixture having an average molecular weight of about 180 to 220.

11. A continuous extractive distillation process for the continuous distillation of an impure propylene oxide feedstock contaminated with water, methanol and acetone and containing about 0.4 to about 1.5 wt. % of acetone in an extractive distillation column fitted with a reboiler and a reflux condenser to remove oxygenated contaminants, including water, methanol and acetone from the impure propylene oxide which comprises the steps of:

continuously introducing said impure propylene oxide feedstock into the lower half of an extractive distillation column containing at least 25 theoretical plates, continuously maintaining predetermined distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in said distillation column below the point of introduction of said feedstock, continuously introducing a recycle stream of an oxyalkylene glycol extractive distillation agent having a molecular weight of not more than about 600 into said extractive distillation column at a point at least 4 theoretical plates above the point of introduction of said impure propylene oxide feedstock, said extractive distillation agent being introduced into said extractive distillation column in the ratio of feedstock to said extractive distillation agent of from about 1:1 to about 20:1, continuously withdrawing a lighter distillation fraction from the reflux condenser of said extractive distillation column consisting essentially of anhydrous propylene oxide contaminated with trace quantities of said acetone and methanol, continuously withdrawing a heavier distillation fraction from the reboiler of said extractive distillation column containing substantially all of said oxyalkylene glycols, water, acetone and methanol introduced into said extractive distillation column, separately continuously distilling said heavier distillation fraction and added oxyalkylene glycol extractive distillation agent to provide an overhead discard distillation fraction comprising methanol, acetone and water and a higher boiling recycle stream comprising said extractive distillation agent, purging a minor amount of said recycle stream and charging the remainder to said extractive distillation column as said recycle stream, continuously monitoring one of said distillation conditions in said acetone buffer zone to detect an upset, and separately adding additional acetone to said impure propylene oxide feedstock being fed to said extractive distillation column in response to an upset in said distillation conditions in an amount sufficient to maintain or restore said acetone buffer zone.

12. An extractive distillation process as in claim 11 wherein the predetermined distillation conditions monitored in said extractive distillation column is temperature.

13. An extractive distillation process as in claim 11 wherein the predetermined distillation conditions monitored in said extractive distillation column is pressure.

14. An extractive distillation process as in claim 11 wherein the predetermined distillation conditions monitored in said extractive distillation column is acetone feed concentration.

15. An extractive distillation process as in claim 11 wherein the extractive distillation agent consists essentially of a mixture of propylene oxide adducts of oxyethylene glycols having the formula:

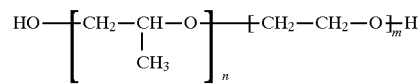

wherein n is a positive integer having a value of 1 to about 4, m is a positive integer having a value of 1 to 3 and the mixture has an average molecular weight of about 250 to 350.

16. An extractive distillation process as in claim 15 wherein the extractive distillation agent consists essentially of a mixture of propylene oxide adducts of ethylene glycol.

17. An extractive distillation process as in claim 15 wherein the extractive distillation agent consists essentially of a mixture of propylene oxide adducts of diethylene glycol.

18. An extractive distillation process as in claim 15 wherein the extractive distillation agent consists essentially of a mixture of propylene oxide adducts of triethylene glycol.

19. An extractive distillation process as in claim 15 wherein the extractive distillation agent consists essentially of a mixture of polyoxypropylene glycols having the formula:

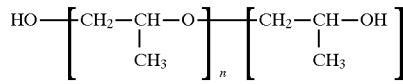

wherein n is a positive integer having a value of 1 to about 4, the mixture having an average molecular weight of about 180 to 220.

* * * * *